US00PP21129P2

(12) United States Plant Patent
Klemm et al.

(10) Patent No.: US PP21,129 P2
(45) Date of Patent: Jun. 29, 2010

(54) ***LOBELIA* PLANT NAMED 'KLELE08623'**

(50) Latin Name: *Lobelia erinus*
Varietal Denomination: KLELE08623

(75) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/384,087

(22) Filed: Mar. 31, 2009

(51) Int. Cl.
*A01H 5/00* (2006.01)

(52) U.S. Cl. ..... Plt./451

(58) Field of Classification Search ..... Plt./451
See application file for complete search history.

*Primary Examiner*—Kent L Bell
(74) *Attorney, Agent, or Firm*—Jondle & Associates, P.C.

(57) ABSTRACT

A new cultivar of *Lobelia* named 'KLELE08623' particularly characterized by vibrant blue flowers, and a uniform and semi-trailing growth habit, is disclosed.

1 Drawing Sheet

Genus and species: *Lobelia erinus*.
Variety denomination: 'KLELE08623'.

BACKGROUND OF THE NEW PLANT

The present invention comprises a new and distinct cultivar of *Lobelia*, botanically known as *Lobelia erinus*, and hereinafter referred to by the cultivar name 'KLELE08623'. 'KLELE08623' originated from a controlled cross made in May 2005 in Stuttgart, Germany between the female *Lobelia* plant, 'KLELE06114' (U.S. Plant Pat. No. 19,680) and the proprietary male *Lobelia* plant, '05 0357' (unpatented). A single plant selection was subsequently chosen for further evaluation and for asexual propagation.

The new cultivar was first propagated in June 2006 by vegetative cuttings in Stuttgart, Germany and has been asexually reproduced repeatedly by vegetative cuttings and in-vitro propagation in Stuttgart, Germany over a three-year period (about five generations). 'KLELE08623' has been found to retain its distinctive characteristics through successive asexual propagations.

Plant Breeder's Rights for this cultivar were applied for in Canada on Mar. 31, 2008. 'KLELE08623' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Vibrant blue flowers; and
2. A uniform and semi-trailing growth habit.

DESCRIPTION OF THE PHOTOGRAPH

This new *Lobelia* plant is illustrated by the accompanying photograph which shows a close-up of the mature flowers, buds and foliage. The colors shown are as true as can be reasonably obtained by conventional photographic procedures. The photograph is of a plant about three months old and grown from rooted cuttings in 10-cm pots in a greenhouse (glasshouse) in Stuttgart, Germany between February to May under conditions which approximate those generally used in commercial practice.

DESCRIPTION OF THE NEW CULTIVAR

The following detailed descriptions set forth the distinctive characteristics of 'KLELE08623'. The data which define these characteristics were collected from asexual reproductions carried out in Stuttgart, Germany. The plant history was taken on two-month old plants in 10-cm pots that were pinched once and grown in a greenhouse in the Spring. The color readings were determined under natural light. Color references are to The R.H.S. Colour Chart of The Royal Horticultural Society of London (R.H.S.) (2001).

DESCRIPTION OF THE NEW PLANT

Classification:
- *Family.*—Campanulaceae.
- *Genus and species.*—*Lobelia erinus.*
- *Common name.*—*Lobelia.*

Parentage:
- *Female parent.*—The *Lobelia* plant 'KLELE06114' (U.S. Plant Pat. No. 19,680).
- *Male parent.*—The proprietary *Lobelia* plant '05 0357' (unpatented).

Plant:
- *Growth and branching habit.*—Medium vigor, good branching.
- *Form.*—Semi-trailing.
- *Height* (*measured from the top of the soil, including any flowers*).—13.0 cm.
- *Width* (*horizontal plant diameter, including any flowers*).—27.0 cm.
- *Time to produce a finished flowering plant.*—9 weeks.
- *Outdoor plant performance.*—Good.
- *Time to initiate roots.*—3 weeks.
- *Root description.*—Fine, white, moderate branching.

Stems:
- *Length.*—About 20.0 cm.
- *Diameter.*—0.15 cm.

*Internode length.*—2.0 cm to 4.0 cm.
*Color.*—RHS 137A.
*Texture.*—Smooth, moderately ribbed.
*Stem anthocyanin.*—Absent.
*Peduncle.*—Color: RHS 141A. Length: 2.0 cm to 3.0 cm. Diameter: 0.03 cm to 0.05 cm. Texture: Smooth.

Leaves:
*Arrangement.*—Alternate.
*Attachment.*—Sessile.
*Color, immature leaf (both surfaces).*—RHS 141A.
*Color, mature leaf.*—Upper surface: Between RHS 141A and RHS 137A. Lower surface: RHS 137C.
*Length.*—Basal leaves are 3.5 cm to 4.5 cm and upper leaves are about 1.0 cm.
*Width.*—Basal leaves are 0.7 cm to 1.0 cm and upper leaves are 0.1 cm to 0.2 cm.
*Shape.*—Basal leaves are lanceolate and upper leaves are narrow lanceolate.
*Margin.*—Basal leaves are serrate and upper leaves are entire.
*Apex.*—Basal leaves are obtuse and upper leaves are acuminate.
*Base.*—Acute.
*Texture (both surfaces).*—Smooth.
*Venation pattern.*—Pinnate.
*Venation color.*—RHS 144C.

Flower bud:
*Shape.*—Inverse drop.
*Diameter.*—0.4 cm to 0.6 cm.
*Length.*—1.0 cm to 1.2 cm.
*Color when bud is first starting to open.*—Greenish white to bluish.

Inflorescence:
*Blooming habit.*—Continuous.
*Lastingness of individual blooms on plant.*—5 to 8 days.
*Fragrance.*—Absent.
*Inflorescence type.*—Raceme.
*Quantity of flowers and buds per flowering branch.*—10 to 15.

Flowers:
*Flower diameter (horizontal).*—About 1.8 cm.
*Flower height (vertical).*—About 1.6 cm.
*Immature flower.*—Color: Upper lobe: Upper surface: RHS 95B. Lower surface: RHS 95C. Lower lobe: Upper surface: RHS 95B. Lower surface: RHS 95C.
*Mature flower.*—Upper lobe: Color: Upper surface: RHS 95B. Lower surface: RHS 95C. Length: About 1.0 cm. Width: About 0.7 cm. Shape: Obovate. Apex: Obtuse. Margin: Entire. Texture (both surfaces): Smooth. Lower lobe: Color: Upper surface: RHS 95B. Lower surface: RHS 95C. Length: About 0.7 cm. Width: About 0.2 cm. Shape: Obovate. Apex: Obtuse. Margin: Entire. Texture (both surfaces): Smooth.
*Corolla.*—Color: Inside: White RHS NN155D (2007RHS Colour Chart) with RHS 95C blue spots. Outside: RHS 95C. Tube length: About 1.0 cm. Diameter: 0.3 cm.
*Calyx.*—Sepals: Color (both upper and lower surfaces): RHS 137A. Length: About 1.0 cm. Diameter: About 1.5 cm. Shape: Funnel, star-shaped (sepals are fused in the lower half). Apex: Acute. Texture: Smooth.

Reproductive organs:
*Androecium.*—Number of anthers: 5. Filament length: About 0.7 cm. Pollen color: Dark yellow. Pollen amount: Abundant.
*Gynoecium.*—Pistil length: About 0.5 cm. Stigma color: Dark violet. Style color: Bluish violet. Style length: About 1.0 cm.

Fruit and seed set: Seeds are small, round, 0.05 cm wide and dark in color (brown to black).

Disease and insect resistance: No particular disease or insect resistance observed.

COMPARISON WITH PARENTAL AND COMMERCIAL CULTIVARS

'KLELE08623' differs from the female parent, the *Lobelia* 'KLELE06114' (U.S. Plant Pat. No. 19,680) in that 'KLELE08623' has vibrant blue (RHS 95B) flowers, a semi-trailing growth habit, and a medium vigor, while 'KLELE06114' has violet (RHS 94A) flowers, a trailing growth habit, and a higher vigor.

'KLELE08623' differs from the male parent, the proprietary *Lobelia* '05 0357' (unpatented) in that 'KLELE08623' has vibrant blue flowers and a semi-trailing growth habit, while '05 0357' has pink flowers and an upright growth habit.

'KLELE08623' differs from the commercial comparison variety, 'KLELE06116' (U.S. plant application Ser. No. 12/002,492, Now Abandoned) in that 'KLELE08623' has small, vibrant blue (RHS 95B) flowers and a semi-trailing growth habit, while 'KLELE06116' has larger, blue (RHS 99D) flowers and a more upright growth habit.

We claim:

1. A new and distinct cultivar of *Lobelia* plant named 'KLELE08623' as shown and described herein.

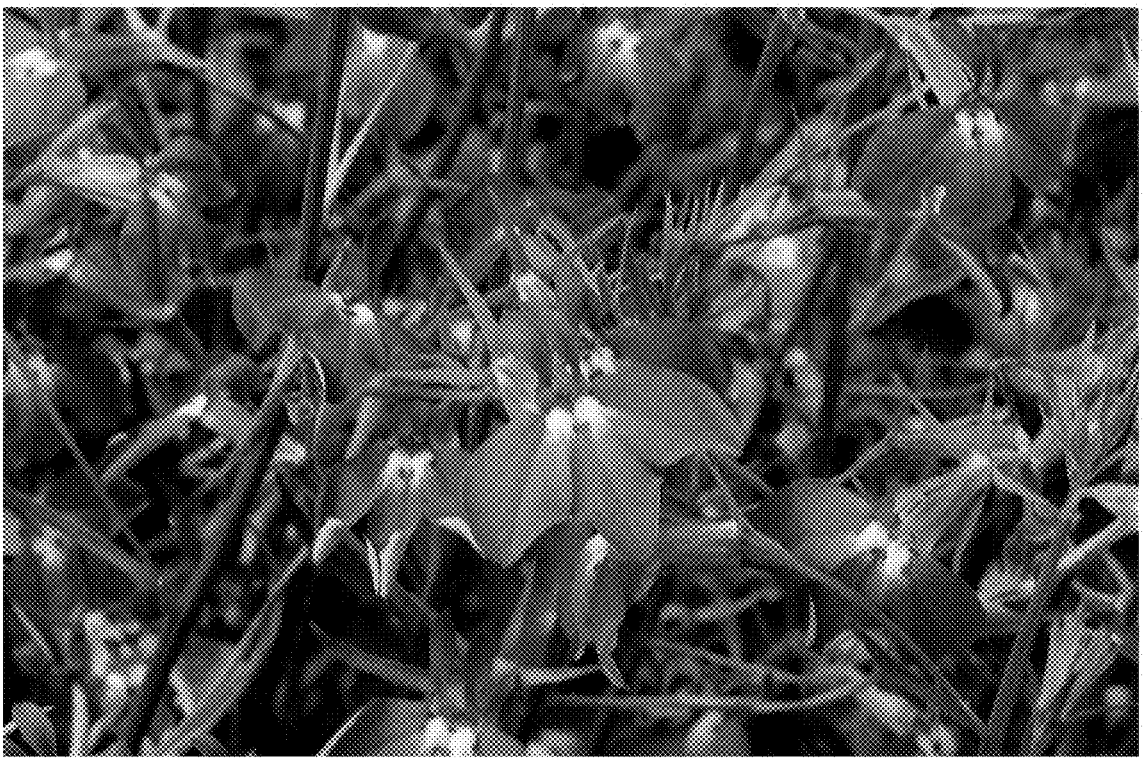

* * * * *